United States Patent [19]

Kawauchi et al.

[11] Patent Number: 4,645,755

[45] Date of Patent: Feb. 24, 1987

[54] FISH GROWTH HORMONE

[75] Inventors: Hiroshi Kawauchi, Iwate; Kazuo Yamaguchi, Sagamihara; Kunikatsu Shirahata, Komae, all of Japan

[73] Assignee: Kyowa Hakko Kogyo Co., Ltd., Tokyo, Japan

[21] Appl. No.: 719,888

[22] Filed: Apr. 4, 1985

[30] Foreign Application Priority Data

Apr. 6, 1984 [JP] Japan ................................. 59-68670

[51] Int. Cl.$^4$ ........................ A61K 37/36; C07K 7/10
[52] U.S. Cl. ...................................... 514/12; 530/324
[58] Field of Search ................... 260/112.5 R; 514/12; 530/324

[56] References Cited

PUBLICATIONS

Dis. Abstr. B 39 (10) 4769–70 (Zoology).
Chem. Abstr., vol. 75, (1971) 95853.
Chem. Abstr., vol. 72, (1970) 76128.
Chem. Abstr., vol. 87, (1977) 149071.
Chem. Abstr., vol. 99, (1983) 173177.
Chem. Abstr., vol. 100, (1984) 48883.

*Primary Examiner*—Delbert R. Phillips
*Attorney, Agent, or Firm*—Antonelli, Terry & Wands

[57] ABSTRACT

A fish growth hormone provided by a purified extract obtained from the pituitary gland of a fish belonging to salmonoid; the hormone is a polypeptide having the following physicochemical properties:

(i) amino acid composition: as indicated in Table 1;
(ii) the sequences of 33 amino acids at the N-terminal and 23 amino acids at the C-terminal are as follows:
   N-terminal: H$_2$N-Ile-Glu-Asn-Gln-Arg-Leu-Phe-Asn-Ile-Ala-Val-Ser-Arg-Val-Gln-His-Leu-His-Leu-Leu-Ala-Gln-Lys-Met-Phe-Asn-Asp-Phe-Asp-Gly-Thr-Leu-Leu-
   C-terminal: -Met-His-Lys-Val-Glu-Thr-Tyr-Leu-Thr-Val-Ala-Lys-Cys-Arg-Lys-Ser-Leu-Glu-Ala-Asn-Cys-Thr-Leu-OH;
(iii) molecular weight: about 22,000;
(iv) isoelectric point: 5.6–5.7; and
(v) soluble in an alkaline aqueous solution and hardly soluble or insoluble in neutral and acidic aqueous solutions.

4 Claims, 3 Drawing Figures

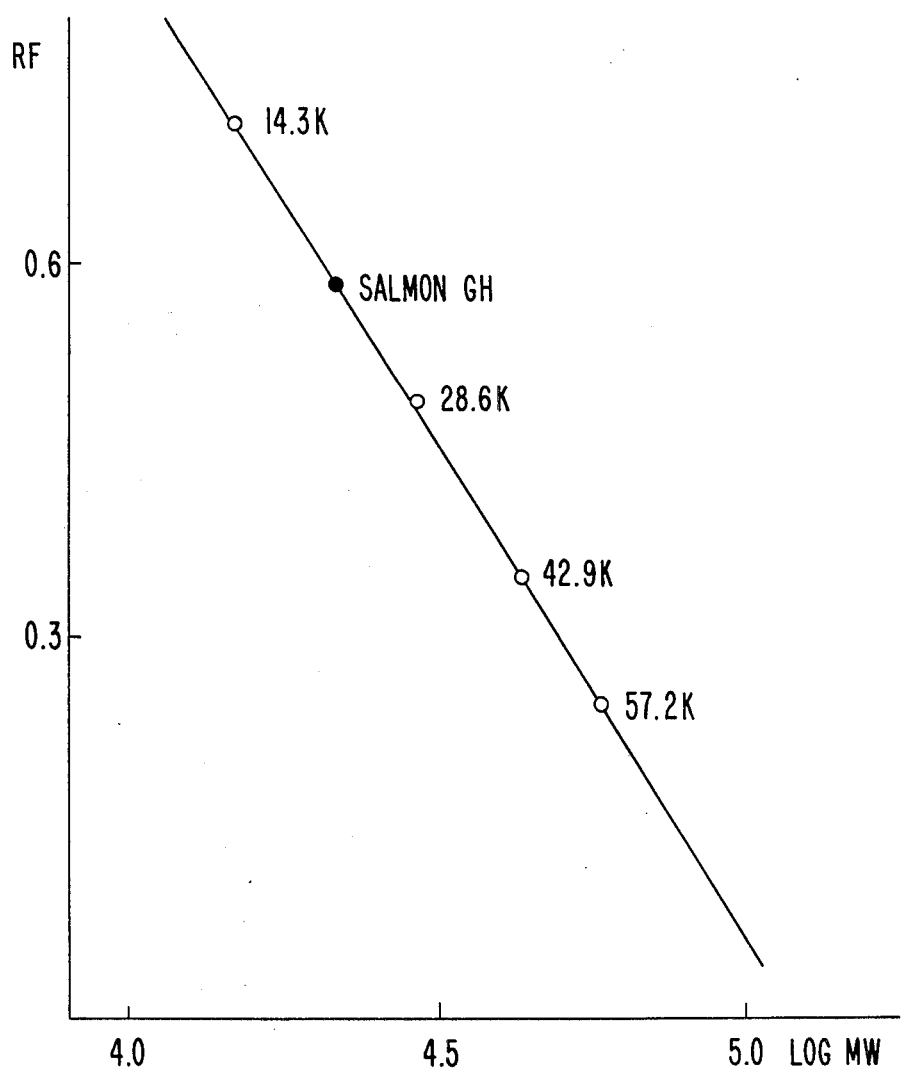

FISH GROWTH HORMONE

The present invention relates to a fish growth hormone derived from a teleost and a process for stimulating growth of a fish using the fish growth hormone.

Mammalian growth hormones are produced in the pituitary gland. The activity and structure of the mammalian growth hormones are known. For example, human growth hormones have been reported in J. Am. Chem. Soc., 80, 4429 (1958) by U. J. Lewis; Biochem. J., 100, 754 (1966) by A. S. Hartree; and Arch. Biochem. Biophys. (Suppl.), 1, 327 (1962) by C. H. Li.

Many reports on the isolation of fish growth hormones have been published as follows:

Isolation from Tilapias
 S. W. Farmer, et al, Gen. Comp. Endocrin., 30, 91 (1976)
Isolation from Sturgeons
 S. W. Farmer, et al, Endocrinology, 108, 377 (1981)
Isolation from Carps
 A. F. Cook, et al, Gen. Comp. Endocrin., 50, 335 (1983)

The present inventors extracted a growth hormone from the salmon pituitary gland, identified it as a polypeptide and found that the molecular weight and amino acid sequences at the N-terminal and the C-terminal of the hormone are similar to those of mammalian growth hormones. Further, the present inventors confirmed that the growth hormone of the present invention is capable of stimulating growth in teleosts. Thus, the present invention has been completed.

BRIEF DESCRIPTION OF THE DRAWINGS

FIG. 3 is the drawing of SDS polyacrylamide electrophoresis whereby the molecular weight of salmon growth hormone was determined according to the migration distance. Standard protein markers No. 44223 2U (product of BDH Chemical Co.) were used. Molecular weights 14.3K, 28.6K, 42.9K and 57.2K correspond to monomer, dimer, trimer and tetramer, respectively.

The present invention is described in greater detail hereinafter.

The present invention relates to a fish growth hormone derived from a teleost and a process for stimulating growth in a fish using the growth hormone.

The fish growth hormone according to the present invention can be extracted from the pituitary gland of a fish belonging to salmonoid with alkaline aqueous solution. Physiocochemical properties of the growth hormone are as follows:

(i) Amino acid composition: as indicated in Table 1.

TABLE 1

| | Amino Acid Composition (Ref. 1) | |
|---|---|---|
| Amino Acid | Salmon Growth Hormone | Tilapia Growth Hormone (Ref. 2) |
| Asp | 28.0 | 19.3 |
| Thr | 6.8 | 12.0 |
| Ser | 11.7 | 21.4 |
| Glu | 22.5 | 29.1 |
| Pro | 3.7 | 6.8 |
| Gly | 7.3 | 7.4 |
| Ala | 6.6 | 8.2 |
| Cys | 3.3 | 4.6 |
| Val | 10.7 | 6.0 |
| Met | 2.7 | 1.2 |
| Ile | 10.6 | 9.0 |
| Leu | 28.5 | 27.2 |
| Tyr | 6.8 | 7.2 |
| Phe | 6.8 | 6.7 |
| Trp | — (Ref. 3) | 1.0 |
| His | 4.2 | 5.0 |
| Lys | 12.6 | 8.2 |
| Arg | 8.6 | 11.0 |

Ref. 1: All values are residues per mole
Ref. 2: The growth hormone isolated from Tilapia, cited from Gen. Comp. Endocrin., 30, 91 (1976).
Ref. 3: As the result of the analysis by ultraviolet absorption, the number of Trp residue per mole was determined as one.

(ii) The sequences of 33 amino acids at the N-terminal and 23 amino acids at the C-terminal are as follows:

N-terminal:

H$_2$N—Ile—Glu—Asn—Gln—Arg—Leu—Phe—Asn—Ile—Ala—
—Val—Ser—Arg—Val—Gln—His—Leu—His—Leu—Leu—Ala—
—Gln—Lys—Met—Phe—Asn—Asp—Phe—Asp—Gly—Thr—Leu—
—Leu—

Figure 1:
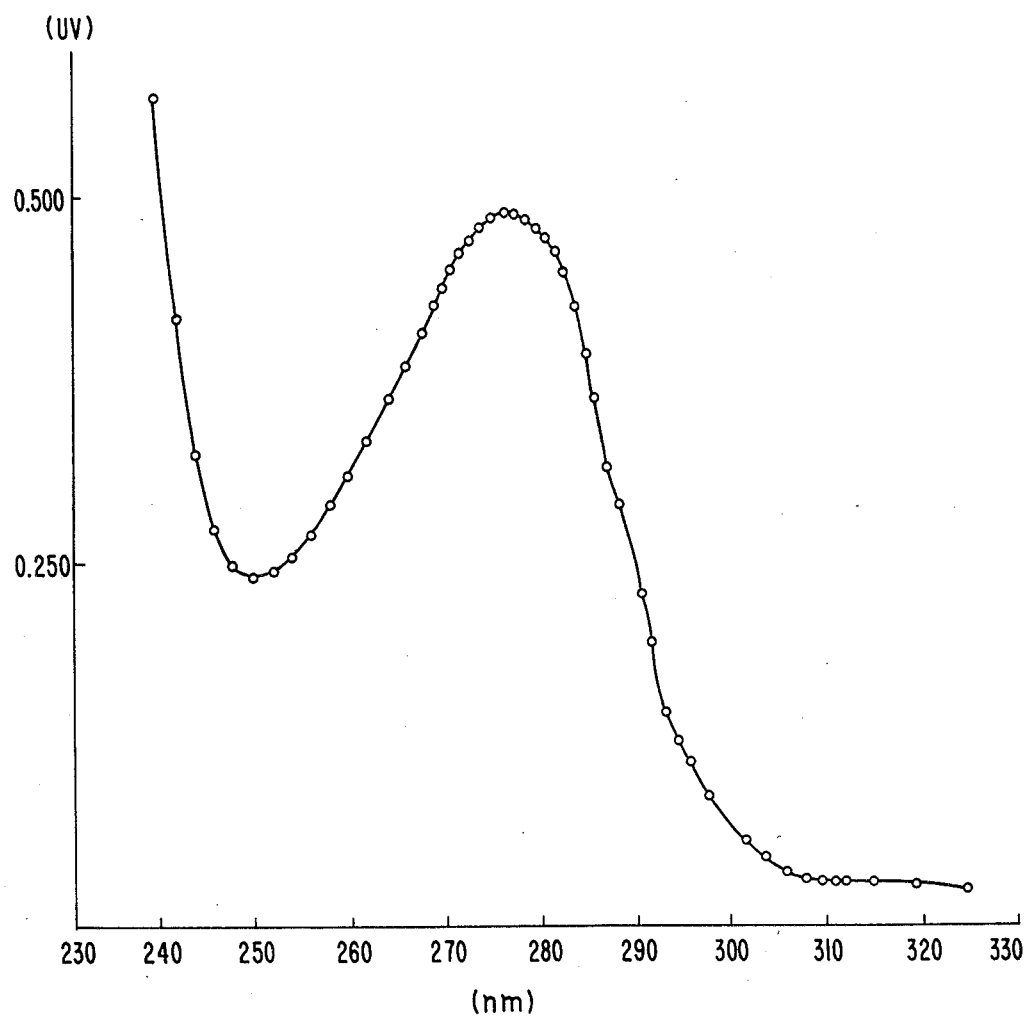
FIG. 1 illustrates an ultraviolet spectrum of the fish growth hormone derived from a teleost.

C-terminal:

—Met—His—Lys—Val—Glu—Thr—Tyr—Leu—Thr—Val—
—Ala—Lys—Cys—Arg—Lys—Ser—Leu—Glu—Ala—Asn—
—Cys—Thr—Leu—OH (iii) Molecular weight: about 22,000
(iv) Ultraviolet absorption spectrum: λmax 277 nm (FIG. 1)
(v) Solubility: Soluble in an alkaline aqueous solution and hardly soluble or insoluble in neutral and acidic aqueous solutions.
(vi) Classification as basic or acidic properties: acidic polypeptide
(vii) Isoelectric point: 5.6–5.7
(viii) Color and form of substance: White powder.
(ix) Polyacrylamide electrophoresis: A single band.

The purity of the salmon growth hormone of the present invention is detected using SDS polyacrylamide electrophoresis (9.9% polyacrylamide/0.1% SDS).

The amino acid composition is analyzed by LKB 4,400 type amino acid autoanalyzer after hydrolyzing the substance at 110° C. for 22 hours in 20% constant boiling point hydrochloric acid. The analysis of amino acid sequences at the N-terminal and the C-terminal of the growth hormone are carried out by the combination of 470A type sequencer (product of Applied Biosystem Co.) and high pressure liquid chromatography (product of Spectra Physics Co.).

The growth hormone of the present invention is prepared by extraction methods with acetone, similar to the conventional method to isolate polypeptides, from the pituitary gland of female Oncorhynchus keta at 3–4 years of age which are swimming and climbing up the river.

For example, a mixed solution of 35% concentrated hydrochloric acid and acetone (10:90–90:10) is added to the pituitary gland and the pituitary gland is ground at 500–2,000 rpm using a homogenizer for 5–20 minutes. The same mixed solution of hydrochloric acid and acetone is added and the mixture is stirred and subjected to centrifugation at 10,000–20,000 rpm under cooling at −5° to 5° C. for 10–60 minutes (the same shall apply hereinafter). The supernatant fluid is removed and 50–90% aqueous acetone is added to the residue. The mixture is stirred and subjected to centrifugation under cooling. The resulting residue is suspended in water and the pH of the suspension is adjusted to between 9–11 with saturated aqueous calcium hydroxide solution. The suspension is stirred and subjected to centrifugation under cooling. The supernatant fluid is dialyzed against water and freeze-dried to obtain a powder. The powder is suspended in water and the pH of the suspension is adjusted to between 5–7 with aqueous NaOH solution. Insoluble material is removed by centrifugation and the pH of the supernatant fluid is adjusted to between 5–6 with hydrochloric acid. The resulting precipitate is recovered by centrifugation.

The precipitate is dissolved in aqueous ammonium acetate solution (pH 8–10, 0.05–0.5M) and subjected to Sephadex column chromatography. Equilibration and elution are carried out with the same aqueous ammonium acetate solution. Active fractions are combined and freeze-dried to obtain a white powder. The white powder is subjected to high pressure liquid chromatography on TSK gel ODS-120T column (product of Toyo Soda Manufacturing CO., LTD.) for final purification. Active fractions are combined and freeze-dried to obtain the growth hormone of the present invention as a white powder. The purity of the growth hormone is about 100%.

The activity of growth hormone is determined by the method described in the following example using rainbow trout (*Salmo irideus*).

It has been found that the growth hormone of the present invention can stimulate growth of teleosts (Osteichthyes) and is useful for the cultivation of Clupeiformes including trouts and salmons. In the case of intraperitoneal injection, 0.01–0.1 μg of the growth hormone per one g of body weight is administered at intervals of 4–7 days.

A specific embodiment of the present invention is illustrated by the following example.

EXAMPLE (1) Extraction and purification of the growth hormone of *Oncorhynchus keta*:

In this step, 50 ml of a mixed solution of 35% concentrated hydrochloric acid and acetone (1:28) was added to 50 g of the pituitary gland of female *Oncorhynchus keta* at 3–4 years of age and the pituitary gland was ground at 1,000 rpm for 10 minutes using a homogenizer. Then, 250 ml of the same mixed solution of hydrochloric acid and acetone as mentioned above was added and the mixture was stirred at 0° C. for one hour and subjected to centrifugation at 15,000 rpm under cooling at −4° C. for 30 minutes. The supernatant fluid was removed and 300 ml of 80% aqueous acetone solution was added to the residue. The mixture was stirred at 0° C. for one hour and subjected to centrifugation under cooling in the same manner as mentioned above. The resulting residue was suspended in 300 ml of water and the pH of the suspension was adjusted to 10 with saturated aqueous calcium hydroxide solution. The suspension was stirred at 4° C. for one hour and subjected to centrifugation under cooling by the same method as mentioned above to obtain a supernatant fluid. The supernatant fluid was dialyzed against water and freeze-dried to obtain about 850 mg of a powder. The powder was suspended in 250 ml of water and the pH of the suspension was adjusted to 10.3 with 0.1N aqueous NaOH solution. Insoluble material was removed by centrifugation and the pH of the supernatant fluid was adjusted to 5.66 with 0.1N hydrochloric acid. The resulting precipitate was recovered by centrifugation. The precipitate was resuspended in 250 ml of water and the same subsequent procedures as mentioned above was repeated to obtain 60 mg of a precipitate.

Figure 2:
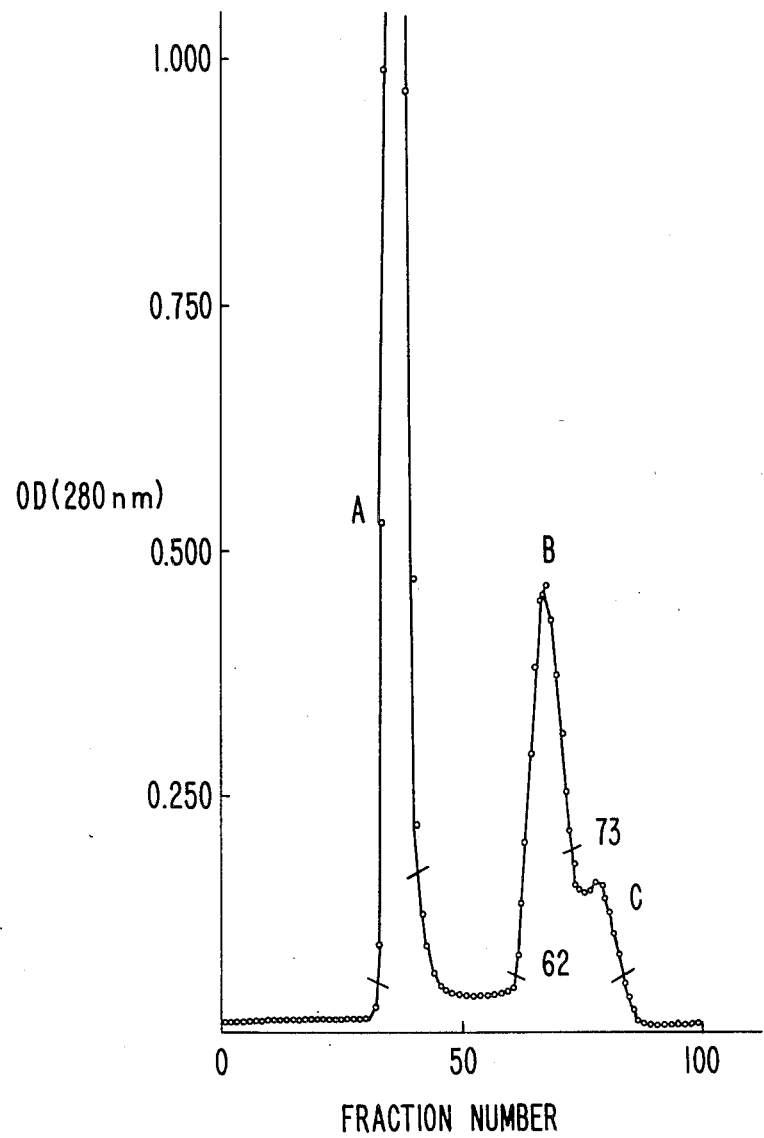
FIG. 2 illustrates the elution pattern which was obtained by treating the pituitary gland of O. keta with a mixed solution of hydrochloric acid and acetone, extracting the treated pituitary gland with alkaline aqueous solution and subjecting the pituitary extracts to fractionation by Sephadex G-25 column.

The precipitate was dissolved in 2 ml of 0.1M aqueous ammonium acetate solution (pH 9.0) and passed through a Sephadex G-75 column (1.9φ × 66 cm) equilibrated with 0.1M aqueous ammonium acetate solution (pH 9.0). Elution was carried out with the same aqueous ammonium acetate solution as mentioned above and the eluate was recovered in 2 ml each of fractions. Fractions under the peak B illustrated in FIG. 2 were combined, dialyzed and freeze-dried to obtain 20 mg of a white powder. Then, 0.5 mg of the white powder was dissolved in 100 μl of 0.1% trifluoroacetic acid solution containing 1M urea and injected in the gel of TSK gel ODS-120T column. Elution was carried out using 20–60% (V/V) acetonitrile containing 0.1% trifluoroacetic acid at a flow rate of 1 ml/min. at 40° C. for 40 minutes. Detection of the growth hormone was conducted at 220 nm. The growth hormone was eluted with 55% acetonitrile. The eluate was freeze-dried to obtain about 0.4 mg of a white powder which is the growth hormone polypeptide of about 100% purity.

(2) Determination of molecular weight:

The growth hormone mentioned above was developed on SDS polyacrylamide gel electrophoresis (9.9% polyacrylamide/0.1% SDS). Calibration curve was obtained using standard protein markers of BOH Chemicals as standard proteins (molecular weight 143,000, 286,000, 429,000 and 572,000) and the molecular weight was calculated as about 22,000 using the calibration curve shown in FIG. 3. The growth hormone was detected as a single band.

(3) Analysis of the sequences of N-terminal and C-terminal amino acids:

In this step, 40 μg of the growth hormone obtained from *Oncorhynchus keta* was dissolved in 0.1% aqueous sodium lauryl sulfate and N-terminal was analyzed by 470A sequencer (applied Biosystem Co.) and SP8000 high pressure liquid chromatography (Specta Physics Co.) to determine the following sequences from the first to the 33rd (N-terminal), and also the sequence of the C-terminal amino acid residues was determined after degradation of the growth hormone with cyanogen bromide and purification of a fragment which contains the C-terminal.

N-terminal:

$H_2N$—Ile—Glu—Asn—Gln—Arg—Leu—Phe—Asn—Ile—Ala—
—Val—Ser—Arg—Val—Gln—His—Leu—His—Leu—Leu—Ala—
—Gln—Lys—Met—Phe—Asn—Asp—Phe—Asp—Gly—Thr—Leu—
—Leu—.

C-terminal:

—Met—His—Lys—Val—Glu—Thr—Tyr—Leu—Thr—Val—
—Ala—Lys—Cys—Arg—Lys—Ser—Leu—Glu—Ala—Asn—

—Cys—Thr—Leu—OH (4) Measurement of ultraviolet absorption spectrum:

The ultraviolet absorption spectrum of the growth hormone mentioned above was measured by UVIDEC type-I spectroscope (NIPPON BUNKO Co.) in 0.1M aqueous ammonium acetate solution (pH 9.0). The maximum absorption was at 277 nm.

(5) Determination of fish growth hormone activity:

Rainbow trout weighing 8–10 g at 4–7 months of age after hatch (one group consisting of 5 rainbow trout) were individualized. Five injections of 1 μg each of the growth hormone isolated from *Oncorhynchus keta* pituitary gland, *Oncorphynchus keta* PRL (prolactin) and sodium chloride were made intraperitoneally at 3 day intervals. The rainbow trout were fed in a weight amount of 1.5% of the body weight of the rainbow trout two times per day in the morning and in the evening, and the water was maintained at a temperature of 3.5°–7.5° C. under a 17L:7D light-dark cycle (controlled by irradiation of electric light). The increase in body weights of the rainbow trout in 20 days from the first injection is shown in Table 2.

The result proves that the growth hormone of the present invention stimulates growth of the rainbow trout.

TABLE

| Sample | Amount Injected | Average Body Weight Increased (g) |
| --- | --- | --- |
| Control | | |
| Sodium chloride | 1 μg | 0.83 (± 0.24) |
| *O. keta* PRL | 1 μg | 0.83 (± 0.22) |
| Fish growth hormone | 1 μg | 1.29 (± 0.20) |

What is claimed is:

1. A substantially pure fish growth hormone derived from *Oncorhynchus keta* which is a polypeptide having the following physicochemical properties:
   (i) amino acid composition: as indicated in Table 1;
   (ii) the sequences of 33 amino acids at the N-terminal and 23 amino acids at the C-terminal are as follows:
   N-terminal: H₂N-Ile-Glu-Asn-Gln-Arg-Leu-Phe-Asn-Ile-Ala-Val-Ser-Arg-Val-Gln-His-Leu-His-Leu-Leu-Ala-Gln-Lys-Met-Phe-Asn-Asp-Phe-Asp-Gly-Thr-Leu-Leu-
   C-terminal: -Met-His-Lys-Val-Glu-Thr-Tyr-Leu-Thr-Val-Ala-Lys-Cys-Arg-Lys-Ser-Leu-Glu-Ala-Asn-Cys-Thr-Leu-OH;
   (iii) molecular weight: about 22,000
   (iv) isoelectric point: 5.6–5.7;
   (v) soluble in an alkaline aqueous solution and hardly soluble or insoluble in neutral and acidic aqueous solutions; and
   (vi) Ultraviolet absorption spectrum: λmax 277 (FIG. 1) and which is obtained by treating the pituitary gland of *Oncorhynchus keta* with a mixed solution of 35% hydrochloric acid and acetone (1:28), extracting the treated pituitary gland with 0.1M aqueous ammonium acetate solution (pH 9.0), subjecting the pituitary extracts to factionation by Sephadex G-75 column and high pressure liquid chromatography, and freeze-drying active fractions having an ability to promote the growth of fish.

2. A composition including the fish hormone defined by claim 1 and carrier suitable for stimulating growth of fish.

3. A process for stimulating growth of fish which comprises administering to the fish a substantially pure fish growth hormone derived from *Oncorhynchus keta* which is a polypeptide having the following physicochemical properties:
   (i) amino acid composition: as indicated in Table 1;
   (ii) the sequences of 33 amino acids at the N-terminal and 23 amino acids at the C-terminal are as follows:
   N-terminal: H₂N-Ile-Glu-Asn-Gln-Arg-Leu-Phe-Asn-Ile-Ala-Val-Ser-Arg-Val-Gln-His-Leu-His-Leu-Leu-Ala-Gln-Lys-Met-Phe-Asn-Asp-Phe-Asp-Gly-Thr-Leu-Leu-
   C-terminal: -Met-His-Lys-Val-Glu-Thr-Tyr-Leu-Thr-Val-Ala-Lys-Cys-Arg-Lys-Ser-Leu-Glu-Ala-Asn-Cys-Thr-Leu-OH;
   (iii) molecular weight: about 22,000
   (iv) isoelectric point: 5.6–5.7;
   (v) soluble in an alkaline aqueous solution and hardly soluble or insoluble in neutral and acidic aqueous solutions; and
   (vi) Ultraviolet absorption spectrum: λmax 277 (FIG. 1) and which is obtained by treating the pituitary gland of *Oncorhynchus keta* with a mixed solution of 35% hydrochloric acid and acetone (1:28), extracting the treated pituitary gland with 0.1M aqueous ammonium acetate solution (pH 9.0), subjecting the pituitary extracts to factionation by Sephadex G-75 column and high pressure liquid chromatography, and freeze-drying active fractions having an ability to promote the growth of fish.

4. The process according to claim 3, wherein the fish to which the fish growth hormone is administered belong to Clupeiformes.

* * * * *